US011854679B1

United States Patent
McCracken, Jr. et al.

(10) Patent No.: US 11,854,679 B1
(45) Date of Patent: Dec. 26, 2023

(54) MEDICATION INVENTORY SYSTEM INCLUDING MACHINE LEARNING BASED MEDICATION DISCREPANCY DETERMINATION AND RELATED METHODS

(71) Applicant: INMAR RX SOLUTIONS, INC., Ft. Worth, TX (US)

(72) Inventors: James W. McCracken, Jr., Winston Salem, NC (US); Brian Rogers, Greensboro, NC (US); Michael Snellenburg, Winston Salem, NC (US)

(73) Assignee: INMAR RX SOLUTIONS, INC., Ft. Worth, TX (US)

( * ) Notice: Subject to any disclaimer, the term of this patent is extended or adjusted under 35 U.S.C. 154(b) by 385 days.

(21) Appl. No.: 16/395,343

(22) Filed: Apr. 26, 2019

(51) Int. Cl.
*G16H 20/13* (2018.01)
*G16H 30/20* (2018.01)
(Continued)

(52) U.S. Cl.
CPC ............. *G16H 20/13* (2018.01); *G06N 20/00* (2019.01); *G06Q 10/087* (2013.01); *G16H 30/20* (2018.01)

(58) Field of Classification Search
None
See application file for complete search history.

(56) References Cited

U.S. PATENT DOCUMENTS 7,080,755 B2   7/2006   Handfield et al.
7,689,318 B2   3/2010   Draper
(Continued)

FOREIGN PATENT DOCUMENTS

AU    2011224520 A1 * 10/2012 ................ A61J 7/04
CA    2706408 A1 *  7/2008 ............ A61J 7/0481

OTHER PUBLICATIONS

Zia, Beenish. "Electronic Pillbox Logger for People with Parkinson's Disease." Order No. 1497810 Portland State University, 2011. Ann Arbor: ProQuest. Web. Apr. 25, 2023. (Year: 2011).*
(Continued)

*Primary Examiner* — Lena Najarian
(74) *Attorney, Agent, or Firm* — ALLEN, DYER, DOPPELT, + GILCHRIST, P.A.

(57) ABSTRACT

A medication inventory system may include a medication tray that includes partitions defining compartments and having a tray identifier associated therewith, and each compartment may store a respective medication. The system may include an imaging apparatus, and a processor and an associated memory cooperating with the imaging apparatus to determine the tray identifier of the medication tray, and maintain in the memory a desired respective medication within each compartment based upon the tray identifier. A respective medication image of the medication within each compartment may be obtained and machine learning may be used to determine a medication within each compartment based upon the respective medication image. A discrepancy may be determined between the determined medication within each compartment and the desired respective medication within each compartment, and when so, a display notification may be generated that includes a visual indicator corresponding to each compartment determined to have the discrepancy.

18 Claims, 9 Drawing Sheets

(51) Int. Cl.
*G06Q 10/087* (2023.01)
*G06N 20/00* (2019.01)

(56) References Cited

U.S. PATENT DOCUMENTS

| | | | |
|---|---|---|---|
| 8,009,913 B2 | 8/2011 | Greyshock | |
| 2008/0146905 A1* | 6/2008 | Keppel | A61B 90/11 600/407 |
| 2011/0246219 A1 | 10/2011 | Smith et al. | |
| 2012/0330665 A1* | 12/2012 | Berkun | G06K 9/00449 704/260 |
| 2013/0151005 A1* | 6/2013 | Gerold | G07F 17/0092 700/235 |
| 2014/0288952 A1* | 9/2014 | Smith | G06Q 40/08 705/2 |
| 2015/0151051 A1 | 6/2015 | Tsoukalis | |
| 2017/0246083 A1 | 8/2017 | Amano et al. | |
| 2018/0260665 A1 | 9/2018 | Zhang et al. | |
| 2018/0308571 A1* | 10/2018 | Tupler | A61J 7/0481 |
| 2019/0228250 A1* | 7/2019 | Fitzpatrick | G06V 30/153 |
| 2019/0244699 A1* | 8/2019 | Loebig | G06N 20/20 |
| 2020/0402632 A1* | 12/2020 | van Schelven | G06Q 10/30 |

OTHER PUBLICATIONS

Rogers et al., U.S. Appl. No. 16/704,573, filed Dec. 5, 2019.
Mccracken, Jr. et al., U.S. Appl. No. 16/395,353, filed Apr. 26, 2019.

\* cited by examiner

MEDICATION INVENTORY SYSTEM INCLUDING MACHINE LEARNING BASED MEDICATION DISCREPANCY DETERMINATION AND RELATED METHODS

TECHNICAL FIELD

The present invention relates to the field of medicine, and more particularly, to medication inventory systems and related methods.

BACKGROUND

Medications, including controlled substances, medical devices, and/or medical tools may be relatively important for treatment of a patient. Thus, it may be desirable to maintain medications in a relatively orderly and predictable fashion to reduce the amount of time it takes to access these medications, particularly in a time sensitive situation.

A medication tray is often used to provide a specific selection and quantity of medications for a particular medical use case, physician preference, and/or location. A given health care facility hospital may have multiple variations of medication trays in use, each varying in type, amount, and/or placement of medications within the medication tray. Multiple medication trays may be used within a crash cart, which is a wheeled cart for dispensing of medication (e.g., in an emergency). Consequently, health care facility pharmacies may process and manage a relatively large quantity of medication trays used throughout a facility.

Accordingly, the medication trays are typically managed. Contents of the medication trays may be replenished and verified, for example, between uses. The verification may be performed manually and include inspection for recalled, expired, and misplaced medications.

U.S. Patent Application Publication No. 2017/0246083 to Amano et al. is directed to a medicine sorting apparatus. More particularly, Amano et al. discloses a medicine sorting apparatus that includes an identifying part, e.g., based upon a camera, which can identify a direction, a posture and characteristics such as a shape, a size, a type and an expiration date of a medicine, and a storing part for storing the medicine so that the medicine can be taken from the storing part. A determination processing part can determine whether or not the medicine is a target to be treated based on the characteristics of the medicine identified by the identifying part.

U.S. Patent Application Publication No. 2018/026065 to Zhang et al. is directed to a deep learning system for recognizing pills in images. More particularly, the system and method use deep learning, including convolutional neural networks, to identify subject objects in unconstrained user images such as unknown pills. An image of, e.g., a pill, may be captured and subsequently processed using deep learning models to identify the pill. The deep learning models may be optimized to have a small footprint (in terms of computational and memory resources) suitable for a resource-limited device such as a smartphone while retaining a high object recognition accuracy. Each such model may also be run on modified versions of the unconstrained image, for example on color, greyscale, and gradient images, to focus the models on different distinguishing features of the object.

SUMMARY

A medication inventory system may include a medication tray that includes a plurality of partitions defining a plurality of compartments. The medication tray may have a tray identifier associated therewith, and each compartment may be for storing a respective medication. The system may include at least one imaging apparatus; and a processor and an associated memory. The processor and associated memory may be configured to cooperate with the at least one imaging apparatus to determine the tray identifier of the medication tray, and maintain in the memory a desired respective medication within each compartment based upon the tray identifier. The processor and associated memory may also be configured to cooperate with the least one imaging apparatus to obtain a respective medication image of the medication within each compartment, and use machine learning to determine a medication within each compartment based upon the respective medication image. The processor and associated memory may be configured to determine a discrepancy between the determined medication within each compartment and the desired respective medication within each compartment, and when so generate a display notification that includes a visual indicator corresponding to each compartment determined to have the discrepancy.

The system may include a mobile wireless communications device that includes a housing and wireless communications circuitry carried by the housing. The at least one imaging apparatus may be carried by the housing. The processor and associated memory may be carried by the housing, for example.

The system may include a support table to carry the medication tray, and an arm coupled to the support table and configured to carry the at least one imaging apparatus spaced above the support table. The system may include a display coupled to the processor for displaying the display notification, and the display notification may include an image of the medication tray with the corresponding visual indicators overlaid thereon, for example.

The display notification may include a further visual indicator corresponding to each compartment determined to not have a discrepancy, and the further visual indicator and visual indicator may have different visual characteristics. The visual indicator may include one of a textual indicator and a colored indicator, for example.

The processor may be configured to determine whether the respective medication within each compartment has expired based upon the at least one medication image, and when so, generate an expired medication display notification that includes an expired medication visual indicator corresponding to each compartment determined to have expired medication. The processor may be configured to determine whether the respective medication within each compartment has been recalled based upon the at least one medication image, and when so, generate a recalled medication display notification that includes a recalled medication visual indicator corresponding to each compartment determined to have recalled medication, for example.

The tray identifier may include a tray barcode, for example. The respective medications image may include alphanumeric text. The processor may be configured to perform an optical character recognition of the alphanumeric text to determine the respective medication within each of the plurality of compartments, for example.

A method aspect is directed to a method of managing medication in a medication inventory system that includes a medication tray including a plurality of partitions defining a plurality of compartments. The medication tray has a tray identifier associated therewith, and each compartment is for storing a respective medication. The method may include using a processor and an associated memory configured to cooperate with at least one imaging apparatus to determine the tray identifier of the medication tray and maintain in the memory a desired respective medication within each compartment based upon the tray identifier. The method may also include using the processor and associated memory to cooperate with the at least one imaging apparatus to obtain a respective medication image of the medication within each compartment and use machine learning to determine a medication within each compartment based upon the respective medication image. The method may also include using the processor and associated memory to determine a discrepancy between the determined medication within each compartment and the desired respective medication within each compartment, and when so generate a display notification that includes a visual indicator corresponding to each compartment determined to have the discrepancy.

A computer readable medium aspect is directed to a non-transitory computer readable medium for managing medication in a medication inventory system that includes a medication tray including a plurality of partitions defining a plurality of compartments. The medication tray may have a tray identifier associated therewith, and each compartment is for storing a respective medication. The non-transitory computer readable medium may include computer executable instructions that when executed by a processor cause the processor to perform operations. The operations may include cooperating with at least one imaging apparatus to determine the tray identifier of the medication tray and maintaining in a memory a desired respective medication within each compartment based upon the tray identifier. The operations may also include cooperating with the at least one imaging apparatus to obtain a respective medication image of the medication within each compartment, and using machine learning to determine a medication within each compartment based upon the respective medication image. The operations may further include determining a discrepancy between the determined medication within each compartment and the desired respective medication within each compartment, and when so generating a display notification that includes a visual indicator corresponding to each compartment determined to have the discrepancy.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Figure 1:
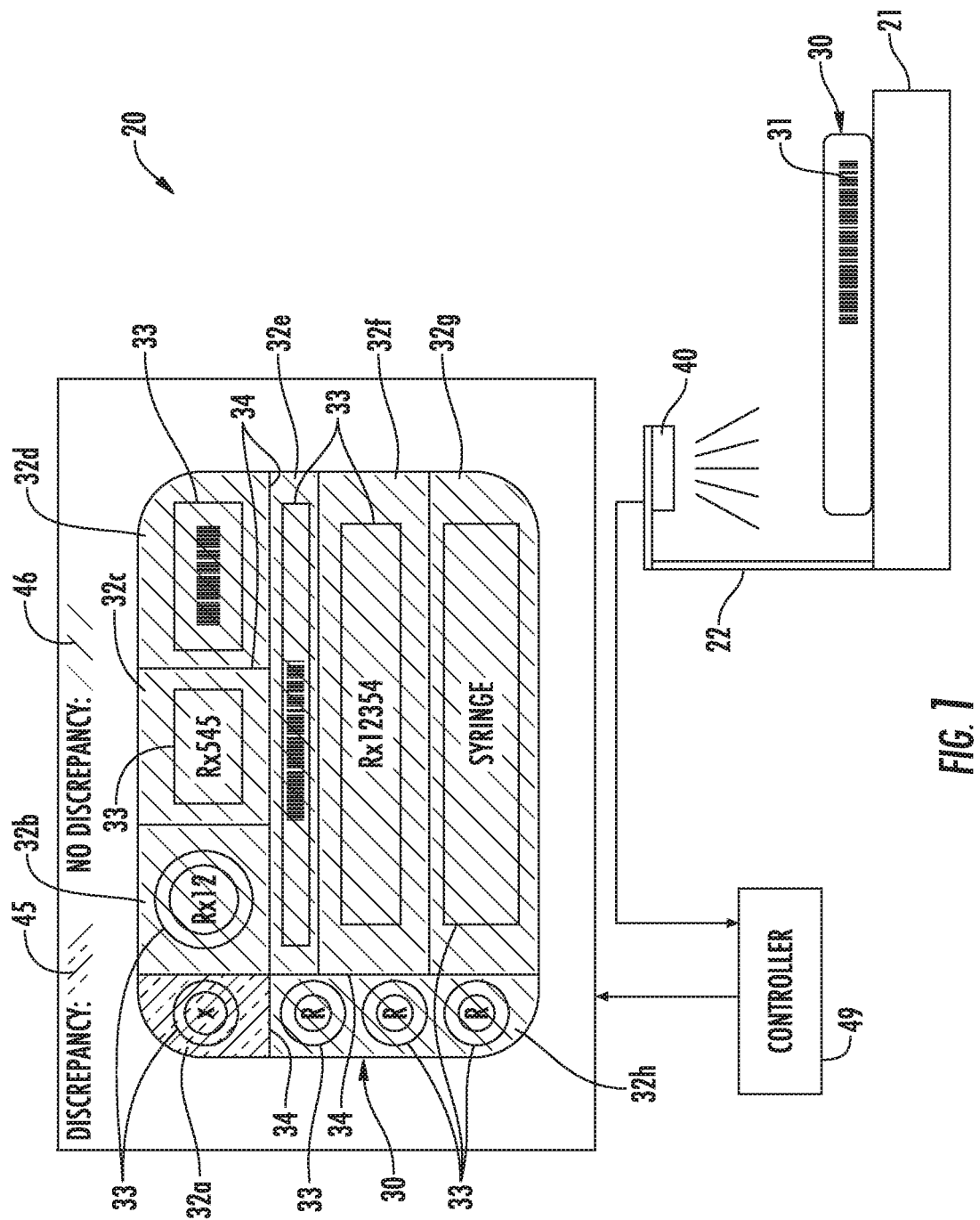
FIG. 1 is a schematic diagram of a medication inventory system according to an embodiment.
Figure 2:
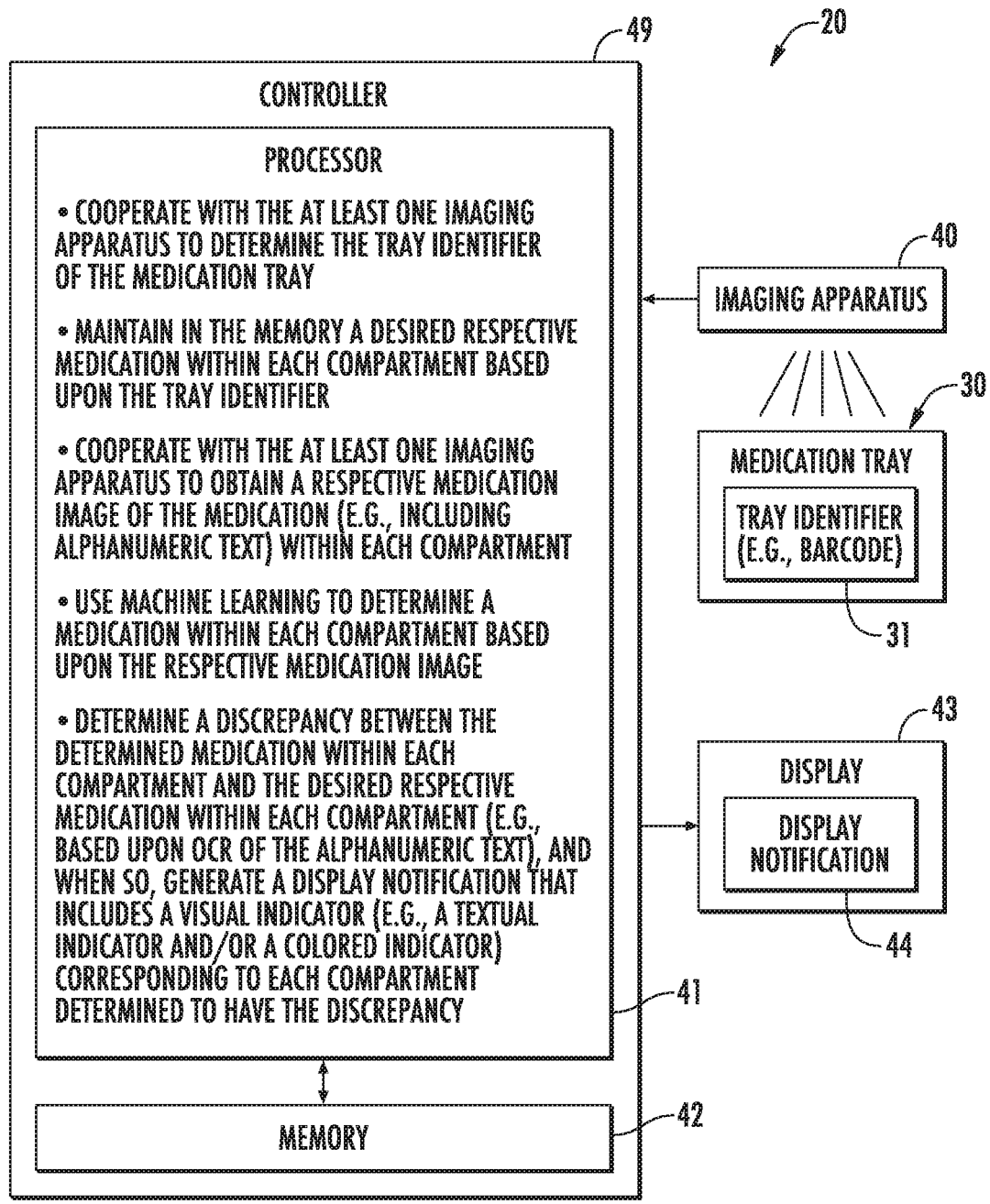
FIG. 2 is a schematic block diagram of the medication inventory system of FIG. 1.

Referring initially to FIGS. 1 and 2, a medication inventory system 20 illustratively includes a medication tray 30. The medication tray 30 includes partitions 34 that define compartments 32a-32h. Each compartment may store a medication 33, multiple medications, a medical or medicated device, a medication container that includes individual medications therein, or other item or substance used for medical treatment. For example, the medication tray 30 may be part of a crash cart, as will be appreciated by those skilled in the art. Of course, the medication tray 30 may be used in other medical environments, for example, an examination room, emergency room, treatment room, operating room, etc.

The medication tray 30 has a tray identifier 31 associated therewith. The tray identifier 31 may be in the form of a barcode, for example, that may be printed or applied (e.g., via an adhesive label) on the medication tray 30. The tray identifier 31 may be in the form of another type of identifier, for example, a quick-response (QR) code, alphanumeric characters, or other optically recognizable and unique code.

The medication inventory system 20 includes a support table 21, for example, in the form of a flat surface, to carry the medication tray 30. In other words, the medication tray 30 may be placed flat on the support table 21, for example, for imaging, as will be described in further detail below. In some embodiments, a support table 21 may not be used.

An arm 22 is coupled to the support table 21 and extends above the support table. The medication inventory system 20 also includes an imaging apparatus 40 carried by the arm 22 and spaced above the support table 21. The arm 22 may be articulating or adjustable (e.g., in height) to accommodate different sized medication trays 30 on the support table 21 and so that the imaging apparatus 40 includes the entire medication tray within its field of view. In some embodiments, the arm 22 may be a fixed arm so that the imaging apparatus 40 is fixedly spaced above the table 21.

The imaging apparatus 40 may be a camera, for example. In some embodiments, there may be more than one imaging apparatus 40, for example, operating together for generating a composite image based upon collected images from each of the imaging apparatuses. The imaging apparatus 40 may be in the form of a handheld scanner, for example. The medication inventory system 20 includes a controller 49. The controller 49 includes a processor 41 and an associated memory 42. The controller 49 may be carried by the support table 21, for example, or in a housing with the imaging apparatus 40. The controller 49 may be remote from the support table 21 and imaging apparatus 40, for example, in a cloud computing environment.

A display 43 is coupled to the controller 49. The display 43 may be carried by or adjacent the support table 21 and/or the arm 22. The display 43 may be remote from the support table 21, for example, a remote display and/or a display of a mobile wireless communications device, such as, for example, a mobile telephone or tablet computer. The controller 49 may be carried within the housing of the display 43. The controller 49 may be located remote from the imaging apparatus 40 and/or display 43, for example, as part of a cloud server in a cloud computing environment.

Figure 3:
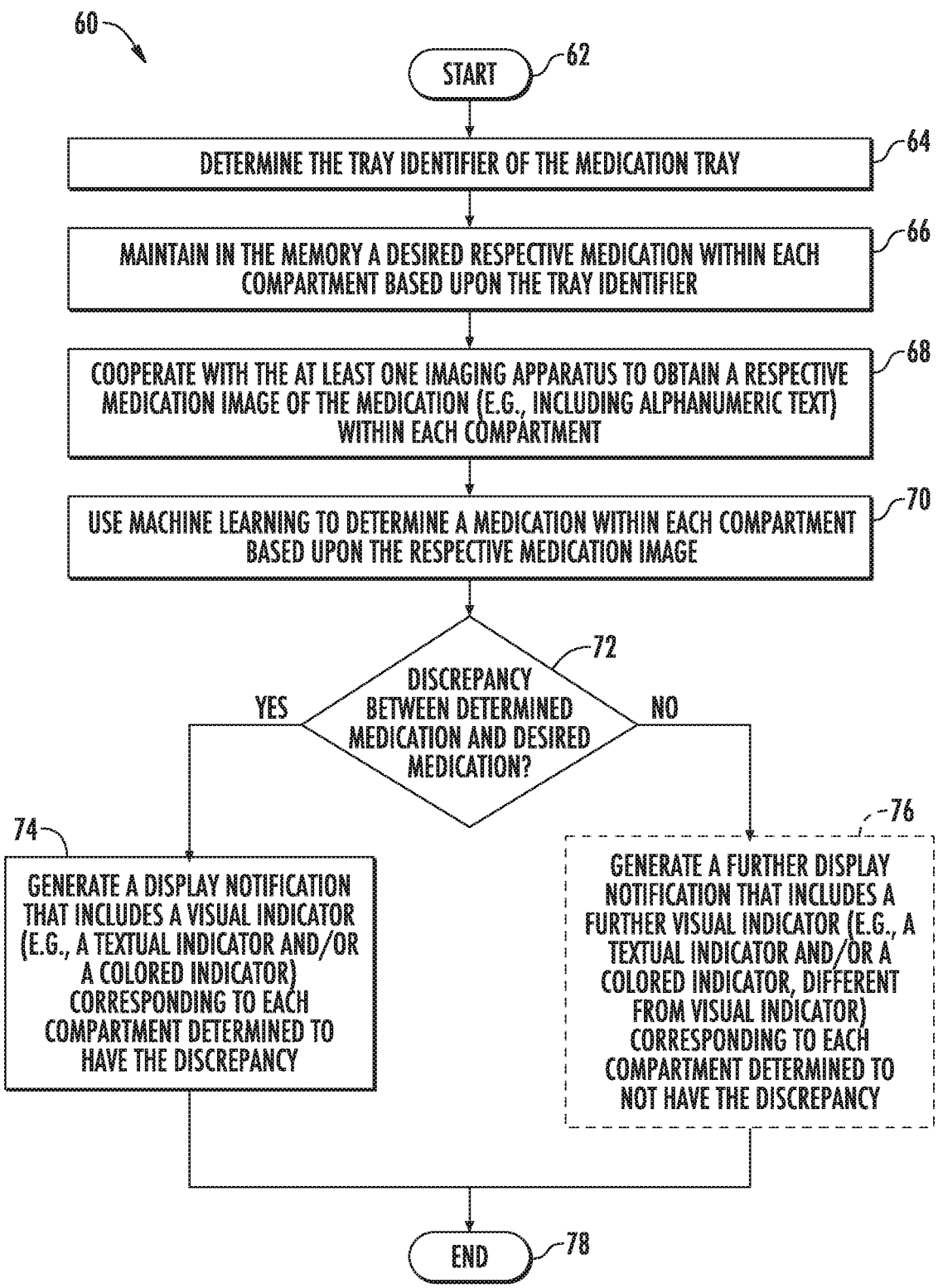
FIG. 3 is a flow diagram of operation of the medication inventory system of FIG. 1.

Referring now to the flowchart 60 in FIG. 3, beginning at Block 62, operations of the medication inventory system 20 will now be described with respect to operations of the controller 49. At Block 64, the controller 49 cooperates with the imaging apparatus 40 to determine the tray identifier of the medication tray. More particularly, the tray identifier 31 is optically sensed or scanned by the imaging apparatus 40. The controller 49 cooperates to identify the particular medication tray 30 based upon the tray identifier 31.

The controller 49 maintains, in the memory 42, a desired respective medication within each compartment 32a-32h based upon the tray identifier (Block 66). More particularly, the memory 42 includes a reference, mapping, or configurations of which medications are desired or expected within each of the compartments 32a-32h for the given tray associated with the tray identifier 31. As will be appreciated by those skilled in the art, a different configuration or expected medication may be within each compartment for different tray identifiers.

At Block 68, the controller 49 cooperates with the imaging apparatus 40 to obtain a respective medication image of the medication 33 within each compartment 32a-32h. More than one medication image may be obtained of a given medication in a corresponding compartment 32a-32h.

The controller 49 uses machine learning to determine a medication 33 within each compartment 32a-32h based upon the respective medication image (Block 70). More particularly, the controller 49 may learn physical characteristics or traits of different medications, for example, as they appear within an obtained medication image, to determine the medication 33. For example, each respective medication image may include alphanumeric text so that the processor 41 may perform an optical character recognition (OCR) of the alphanumeric text to determine the respective medication within each compartment 32a-32h. The alphanumeric text may include a lot number, medication identifier, expiration date, etc. Each respective medication 33 also has a size, shape, and color. The processor 41 may use the size, shape, and color of each medication 33 to determine the medication within each compartment 32a-32h. The processor 41 may also use the orientation, pose, and/or image parameters to determine the medication 33 within each compartment 32a-32h. These physical characteristics may be fed as input to train a learning function. Other input, for example, the alphanumeric text, may be used to train the learning function. Those skilled in the art will appreciate that other factors may be used to train the learning function and thus serve as a basis to determine the medication, such as, for example, physical similarity to other medications, relative position within the medication tray 30, and/or often-confused-for medications. The processor 41 may use other and/or additional recognition techniques, as will be appreciated by those skilled in the art. For example, the processor 41 may use more than one learning function in addition to OCR.

At Block 72, a determination is made as to whether there is a discrepancy between the determined medication 33 within each compartment 32a-32h and the desired respective medication within each compartment. In particular, the determined medication within each compartment 32a-32h is compared or matched to the desired respective medication stored in the memory 42. Those skilled in the art will appreciate that the identifying data from the medication determination may be matched to corresponding stored desired medication data, and/or the obtained images may be matched to reference images of medications 33 stored in the memory 42. A discrepancy may be determined when a threshold amount of matched data is not exceeded. In other words, if the processor 41 cannot determine within a threshold amount of certainty, for example, less than 100%, that the determined medication 33 (as determined based upon machine learning) matches the expected medication for a given compartment, the processor may determine that there is a discrepancy. In other words, a mismatch of medication 33 may be determined.

If at Block 72 it is determined that there is discrepancy between the determined medication within each compartment 32a-32h and the desired respective medication with each compartment, the controller 49 generates a display notification 44 that includes a visual indicator 45 corresponding to each compartment determined to have a discrepancy (Block 74). The display notification 44 may include an image of the medication tray 30 with the corresponding visual indicators 45 overlaid thereon. The display notification 44 may, in some embodiments, also include further visual indicators 46 having one or more different visual characteristics that correspond to each compartment 32a-32h that does not have a discrepancy (Block 76). The visual indicators 45 may be in the form of a textual indictor (e.g., "OK", or "DISCREPANCY") and/or a colored indictor (e.g., a red box overlaid corresponding compartments having a discrepancy and a green box overlaid corresponding compartments not having a discrepancy). Upon a discrepancy, the controller 49 may display or provide an indication of the expected medication, and in some instances recommend a substitute medication (e.g., a generic or similarly performing). Operations end at Block 78. Of course, in some embodiments, if there are no discrepancies, no display notification may be displayed and the operations may end at Block 78.

Figure 4:
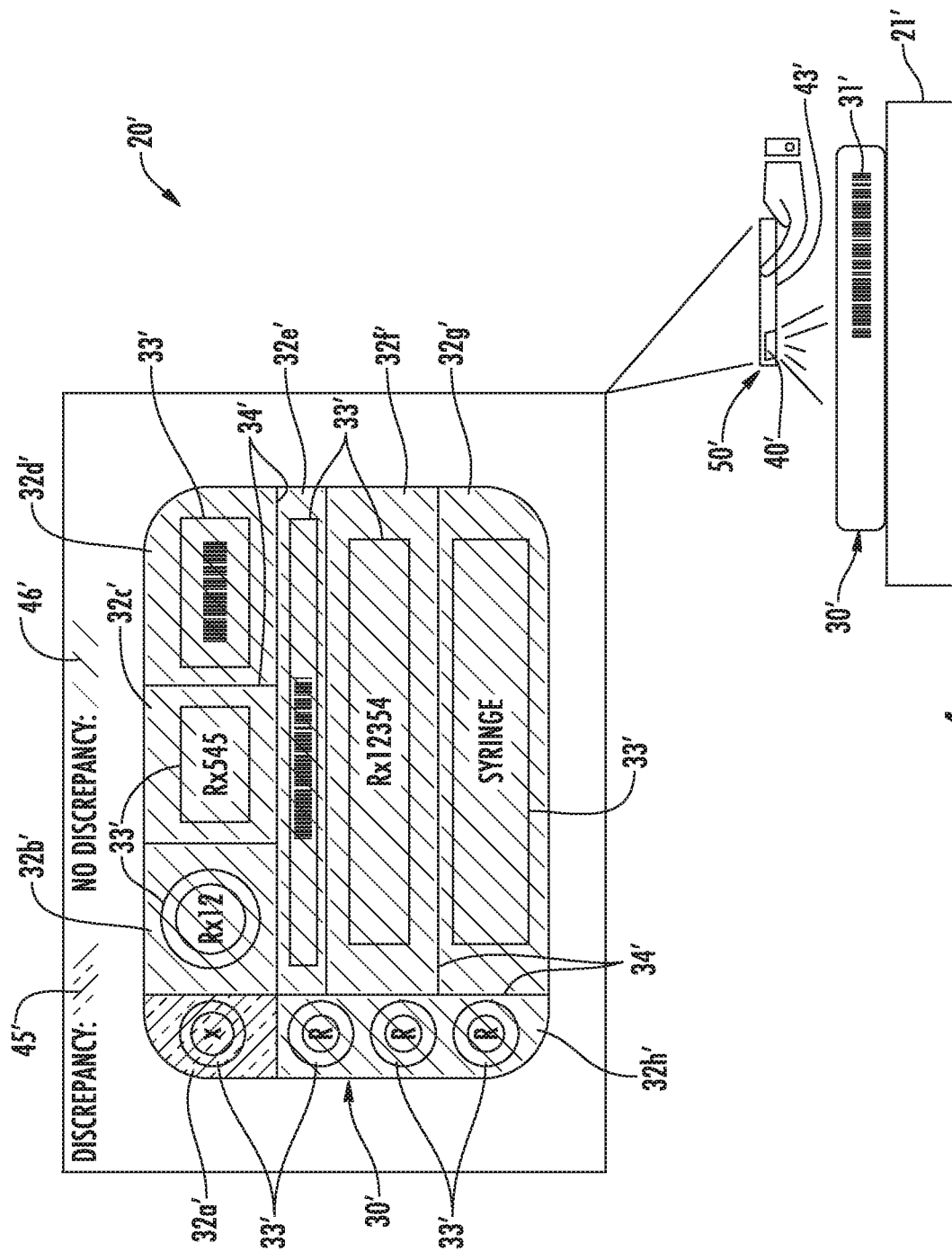
FIG. 4 is a schematic diagram of a medication inventory system according to another embodiment.
Figure 5:
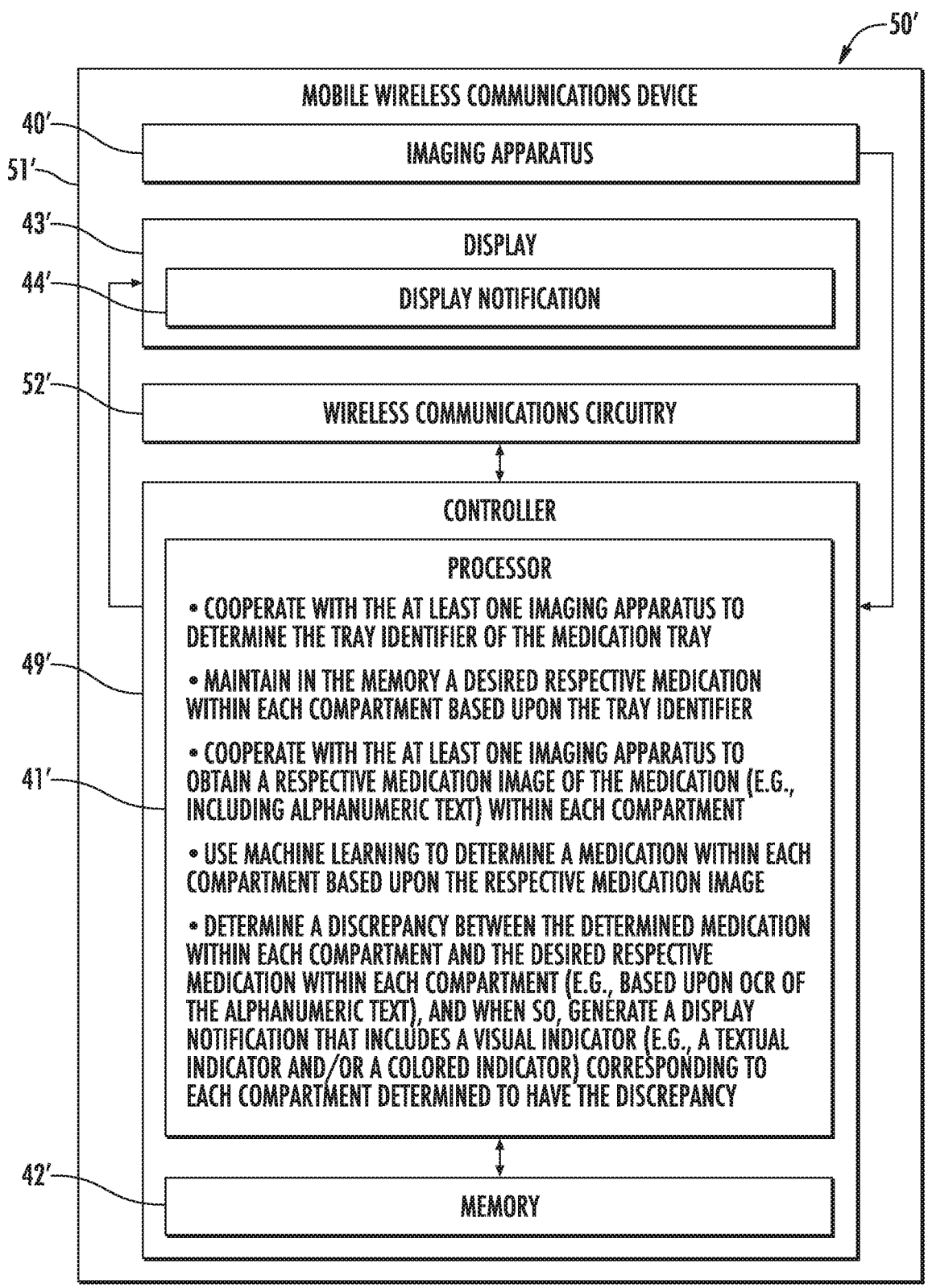
FIG. 5 is a schematic block diagram of the medication inventory system of FIG. 4.

Referring now to FIGS. 4-5, in another embodiment, the medication inventory system 20' includes a mobile wireless communications device 50' that includes a housing 51' and wireless communications circuitry 52' carried by the housing. The mobile wireless communications device 50' may be in the form of a mobile telephone or tablet computer, for example. Of course, the mobile wireless communications device may be in the form of another type of device. The wireless communications circuitry 52' may include long and short-range wireless communications circuitry, for example, cellular, WiFi, near-field communications (NFC), and/or Bluetooth®. The imaging apparatus 40' is also carried by the housing 51' opposite a display 53' also carried by the housing. The controller 49' is also carried by the housing 51'. In the present embodiment, a user associated with the mobile wireless communications device 50' may manually move the mobile wireless communications device over the top of the medication tray 30' with the imaging apparatus 40' pointed toward the medication tray to obtain the respective medication images and the tray identifier 31' (e.g., within the field of view as the mobile wireless communications is moved). The mobile wireless communications device 50' may be carried by or coupled to the arm if the manual movement by the user is not desired. During operation, as the user manually moves the mobile wireless communications device 50' over or across the top of the medication tray 30' acquiring images (imaging device facing the medication tray) any display notifications 44' including corresponding visual indicators 45' may be displayed on the display 53' (facing the user and carried by the housing 51' opposite the imaging device 40').

Figure 6:
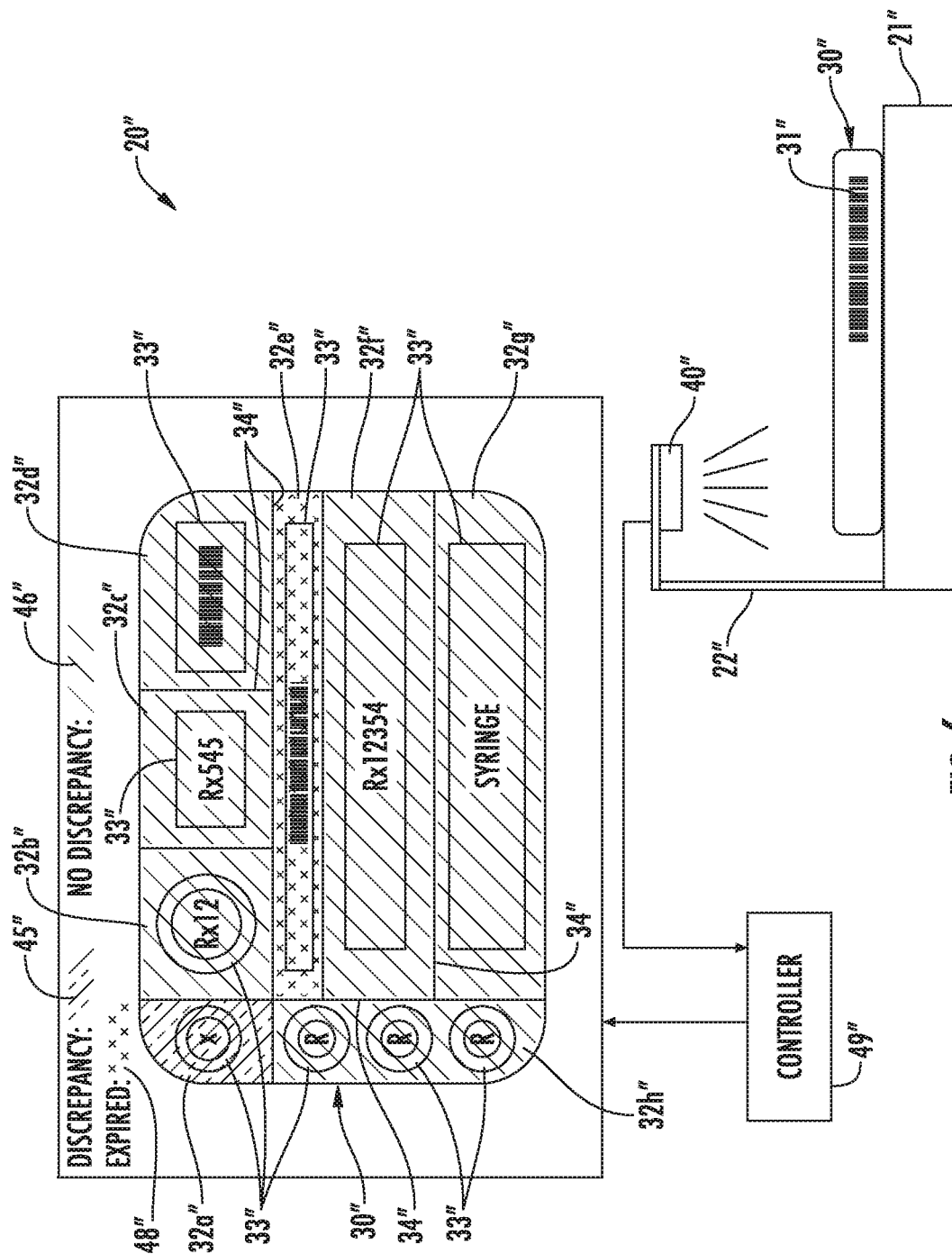
FIG. 6 is a schematic diagram of a medication inventory system according to another embodiment.
Figure 7:
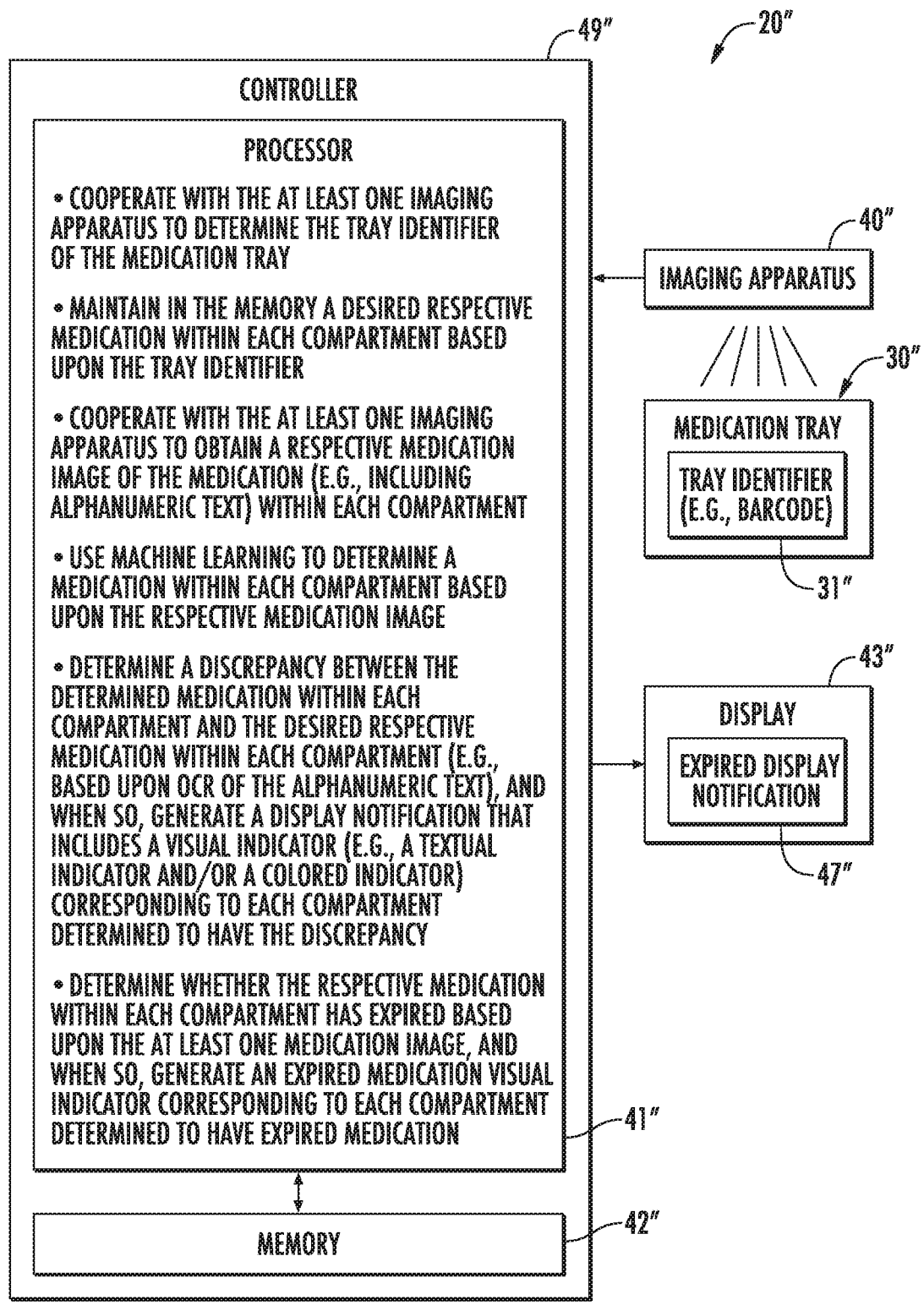
FIG. 7 is a schematic block diagram of the medication inventory system of FIG. 6.

Referring now to FIGS. 6 and 7, in another embodiment, the controller 49″ determines whether the respective medication 33″ within each compartment 32a″-32h″ has expired based upon the medication image. When a respective medication is determined to have expired, the controller 49″ generates an expired medication display notification 47″ that includes an expired medication visual indicator 48″ corresponding to the each compartment determined to have expired medication. The expired medication display notification 47″ may be similar (e.g., colored indicator and/or textual) to the notification described above with respect a determined discrepancy, but may have different visual characteristics. In some embodiments, the expired medication visual indicator 48″ may be integrated within the display notification 44″ of a discrepancy. For example, the visual indicator 45″ included within the display notification 44″ may indicate the type of discrepancy by way of the visual characteristics (e.g., expired, not expected medication).

Figure 8:
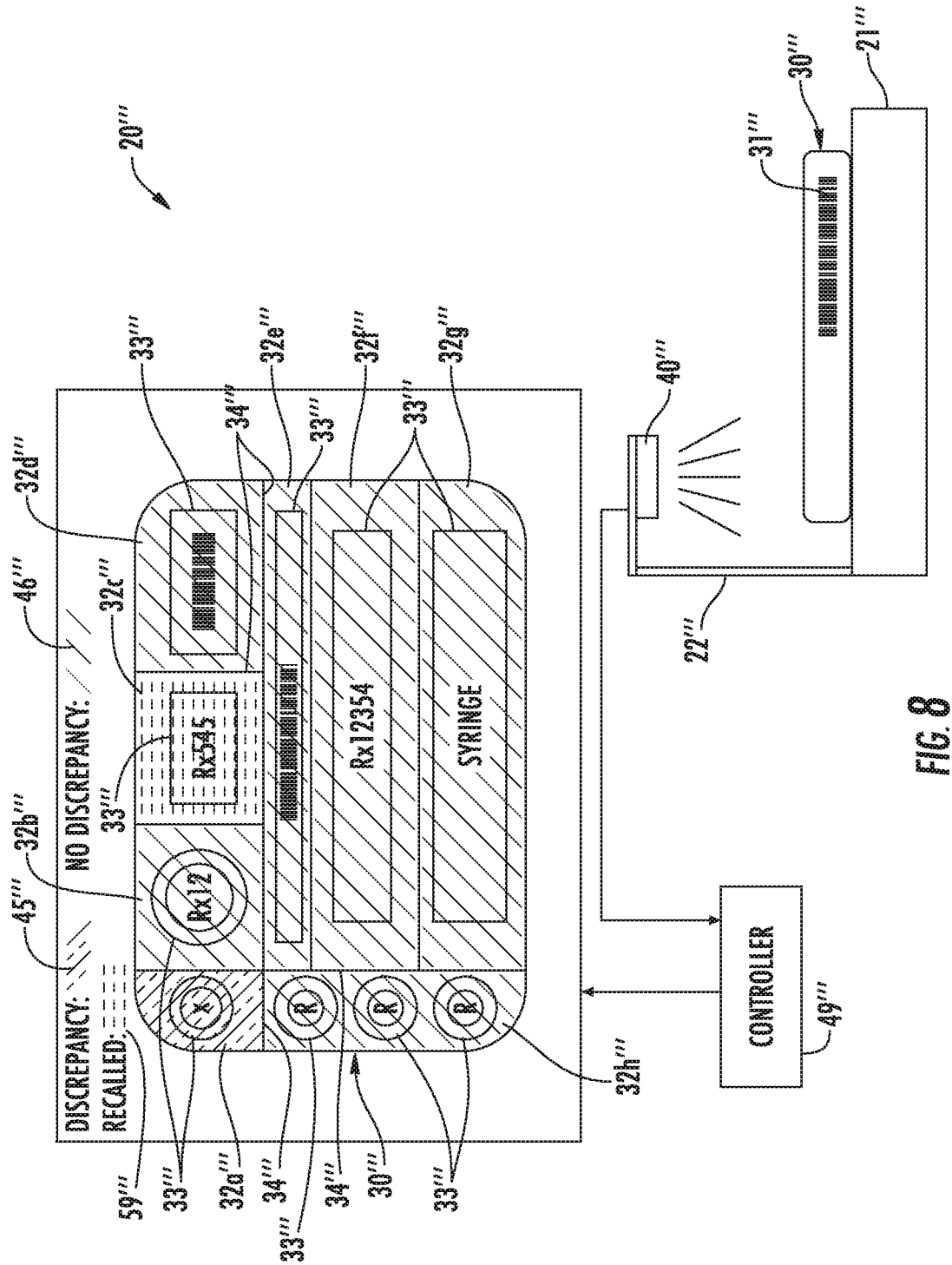
FIG. 8 is a schematic diagram of a medication inventory system according to another embodiment.
Figure 9:
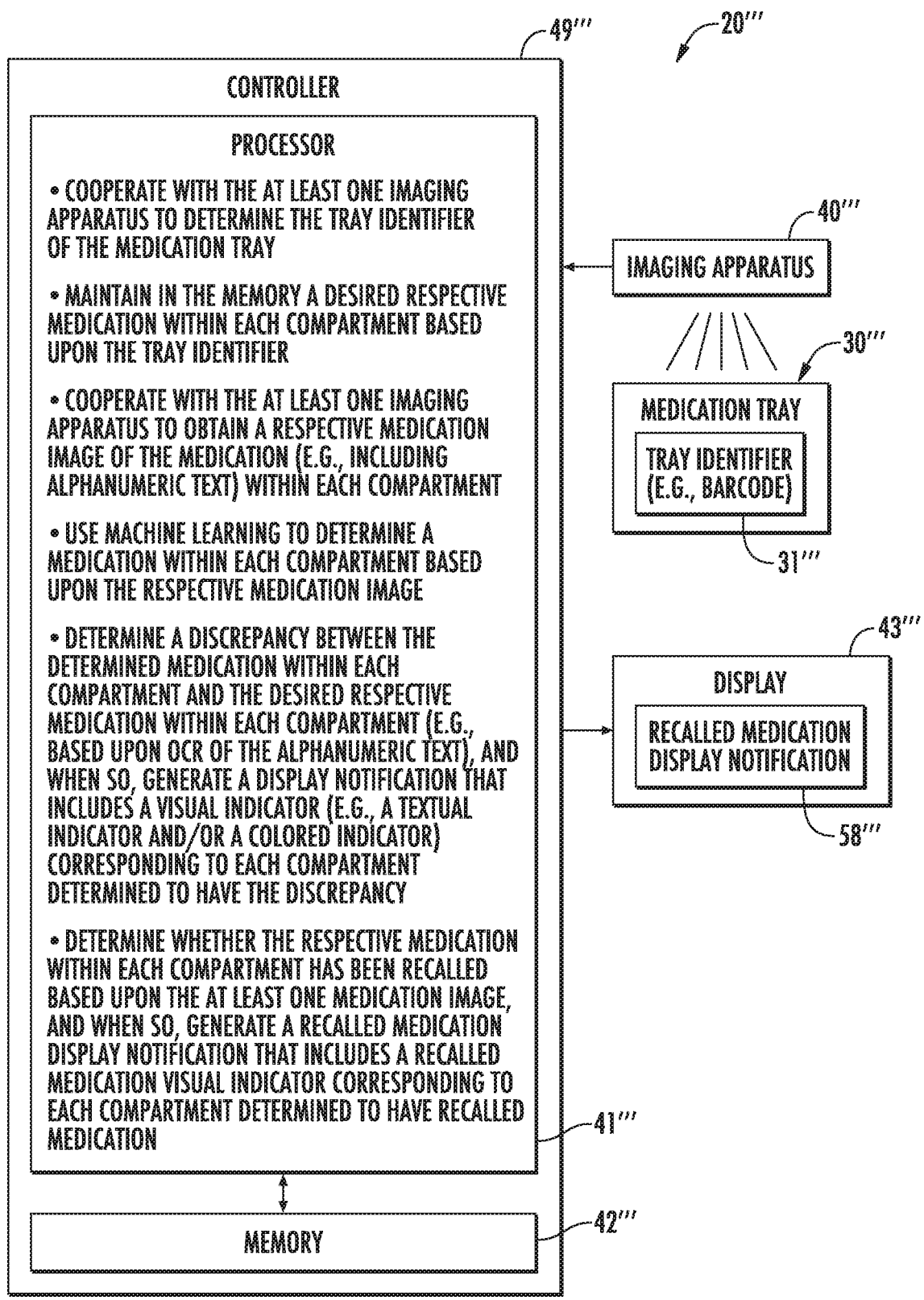
FIG. 9 is a schematic block diagram of the medication inventory system of FIG. 8.

Referring now to FIGS. 8 and 9, in another embodiment, the controller 49‴ determines whether the respective medication within each compartment 32a‴-32h‴ has been recalled based upon the medication image. When a respective medication 33‴ is determined to have been recalled, the controller 49‴ generates a recalled medication display notification 58‴ that includes a recalled medication visual indicator 59‴ corresponding to the each compartment 32a‴-32h‴ determined to have recalled medication. The recalled medication display notification 58‴ may be similar (e.g., colored indicator and/or textual) to the notification 44 described above with respect a determined discrepancy, but may have different visual characteristics. In some embodiments, the recalled medication visual indicator 59‴ may be integrated within the display notification 44 and/or expired medication notification 47″. For example, the visual indicator included within the display notification 44 may indicate the type of discrepancy by way of the visual characteristics (e.g., recalled, not expected medication, expired).

The medication inventory system 20 may be advantageous for providing increased accuracy loading or packing of medication 33 within the compartments 32a-32h of a given medication tray 30. More particularly, the medication inventory system 20 described herein may be particularly advantageous for confirming medications 33 within a crash cart, which typically includes medications for emergency treatment. As will be appreciated by those skilled in the art, items within a crash cart are typically located in the same compartment within a tray among different crash carts within a given hospital or hospital system. Medical professionals may typically, in an emergency situation, reach for a medication 33 within a given compartment without inspection of the medication to confirm the accuracy of the medication within the compartment. Accordingly, a misplaced medication 33 or a discrepancy of what is expected within a compartment and what is actually within the compartment may have far reaching implications. The system 20 described herein may address these shortcomings by providing confirmation that the expected medications match the actual medications within a compartment, and by providing notification when there is a discrepancy.

A method aspect is directed to a method of managing medication in a medication inventory system 20 that includes a medication tray 30 including a plurality of partitions 34 defining a plurality of compartments 32a-32h. The medication tray 30 has a tray identifier 31 associated therewith, and each compartment 32a-32h is for storing a respective medication 33. The method includes using a processor 41 and an associated memory 42 configured to cooperate with at least one imaging apparatus 40 to determine the tray identifier 31 of the medication tray 30 and maintain in the memory a desired respective medication within each compartment based upon the tray identifier. The method also includes using the processor 41 and associated memory 42 to cooperate with the at least one imaging apparatus 40 to obtain a respective medication image of the medication 33 within each compartment 32a-32h and use machine learning to determine a medication within each compartment based upon the respective medication image. The method also includes using the processor 41 and associated memory 42 to determine a discrepancy between the determined medication 33 within each compartment and the desired respective medication within each compartment, and when so generate a display notification 44 that includes a visual indicator 45 corresponding to each compartment determined to have the discrepancy.

A computer readable medium aspect is directed to a non-transitory computer readable medium for managing medication in a medication inventory system 20 that includes a medication tray 30 including a plurality of partitions 34 defining a plurality of compartments 32a-32h. The medication tray 30 may have a tray identifier 31 associated therewith, and each compartment 32a-32h is for storing a respective medication 33. The non-transitory computer readable medium may include computer executable instructions that when executed by a processor 41 cause the processor to perform operations. The operations include cooperating with at least one imaging apparatus 40 to determine the tray identifier 31 of the medication tray 30 and maintaining in a memory 42 a desired respective medication within each compartment 32a-32h based upon the tray identifier 31. The operations also include cooperating with the at least one imaging apparatus 40 to obtain a respective medication image of the medication 33 within each compartment 32a-32h, and using machine learning to determine a medication within each compartment based upon the respective medication image. The operations further include determining a discrepancy between the determined medication 33 within each compartment and the desired respective medication within each compartment, and when so generating a display notification 44 that includes a visual indicator 45 corresponding to each compartment determined to have the discrepancy.

While several embodiments have been described herein, it should be appreciated by those skilled in the art that any element or elements from one or more embodiments may be used with any other element or elements from any other embodiment or embodiments. Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A medication inventory system comprising:
a mobile wireless communications device comprising a housing, a display carried by the housing, and wireless communications circuitry carried by the housing;
a medication tray comprising a plurality of partitions defining a plurality of compartments, the medication tray having a computer-readable tray identifier associated therewith, and each compartment for storing a respective medication;
at least one imaging apparatus carried by the housing; and a processor and an associated memory configured to
cooperate with said at least one imaging apparatus to obtain a tray identifier image and determine the computer-readable tray identifier of the medication tray based upon the tray identifier image,
maintain in the memory a desired respective medication within each compartment based upon the computer-readable tray identifier,
cooperate with said at least one imaging apparatus to obtain a respective compartment image including the medication within each compartment, the respective compartment image comprising alphanumeric text associated with the medication therein,
use machine learning based upon an optical character recognition of the alphanumeric text to determine the medication within each compartment based upon the respective compartment image, and
determine a discrepancy between the determined medication within each compartment and the desired respective medication within each compartment, and upon determining the discrepancy, generate a display notification for display on the display, the display notification including an image of the medication tray including the plurality of compartments and the medications within each compartment and with visual indicators corresponding to each compartment overlaid on each compartment in the image of the medication tray, each visual indicator having one of a first visual characteristic indicative of the discrepancy and a second visual characteristic different than the first visual characteristic indicative of no discrepancy.

2. The system of claim 1 wherein said processor and associated memory are carried by said housing.

3. The system of claim 1 comprising a support table to carry said medication tray, and an arm coupled to said support table and configured to carry said at least one imaging apparatus spaced above said support table.

4. The system of claim 1 wherein each visual indicator comprises one of a textual indicator and a colored indicator.

5. The system of claim 1 wherein said processor is configured to determine whether the respective medication within each compartment has expired based upon the respective compartment image, and upon determining the respective medication has expired, generate an expired medication display notification that includes an expired medication visual indicator corresponding to each compartment determined to have expired medication.

6. The system of claim 1 wherein said processor is configured to determine whether the respective medication within each compartment has been recalled based upon the respective compartment image, and upon determining the respective medication has been recalled, generate a recalled medication display notification that includes a recalled medication visual indicator corresponding to each compartment determined to have recalled medication.

7. The system of claim 1 wherein the computer-readable tray identifier comprises a tray barcode.

8. A medication inventory device for an inventory medication system comprising a medication tray comprising a plurality of partitions defining a plurality of compartments, the medication tray having a computer-readable tray identifier associated therewith, and each compartment for storing a respective medication, the medication inventory device comprising:
at least one imaging apparatus carried by a housing of a mobile wireless communications device; and
a processor and an associated memory configured to
cooperate with said at least one imaging apparatus to obtain a tray identifier image and determine the computer-readable tray identifier of the medication tray based upon the tray identifier image,
maintain in the memory a desired respective medication within each compartment based upon the computer-readable tray identifier,
cooperate with said at least one imaging apparatus to obtain a respective compartment image including the medication within each compartment, the respective compartment image comprising alphanumeric text associated with the medication therein,
use machine learning based upon an optical character recognition of the alphanumeric text to determine the medication within each compartment based upon the respective compartment image, and
determine a discrepancy between the determined medication within each compartment and the desired respective medication within each compartment, and upon determining the discrepancy, generate a display notification for display on a display of the mobile wireless communications device, the display notification including an image of the medication tray including the plurality of compartments and the medications within each compartment and with visual indicators corresponding to each compartment overlaid on each compartment in the image of the medication tray, each visual indicator having one of a first visual characteristic indicative of the discrepancy and a second visual characteristic different than the first visual characteristic indicative of no discrepancy.

9. The medication inventory device of claim 8 comprising wireless communications circuitry carried by the housing.

10. The medication inventory device of claim 8 wherein said processor and associated memory are carried by said housing.

11. The medication inventory device of claim 8 wherein said processor is configured to determine whether the respective medication within each compartment has expired based upon the respective compartment image, and upon determining the respective medication has expired, generate an expired medication display notification that includes an expired medication visual indicator corresponding to each compartment determined to have expired medication.

12. The medication inventory device of claim 8 wherein said processor is configured to determine whether the respective medication within each compartment has been recalled based upon the respective compartment image, and upon determining the respective medication has been recalled, generate a recalled medication display notification that includes a recalled medication visual indicator corresponding to each compartment determined to have recalled medication.

13. A method of managing medication in a medication inventory system comprising a medication tray comprising a plurality of partitions defining a plurality of compartments, the medication tray having a computer-readable tray identifier associated therewith, and each compartment for storing a respective medication, the method comprising:
using a processor and an associated memory configured to
cooperate with at least one imaging apparatus carried by a housing of a mobile wireless communications device to obtain a tray identifier image and determine the computer-readable tray identifier of the medication tray based upon the tray identifier image, maintain in the memory a desired respective medication within each compartment based upon the computer-readable tray identifier, cooperate with the at least one imaging apparatus to obtain a respective compartment image including the medication within each compartment, the respective compartment image comprising alphanumeric text associated with the medication therein, use machine learning based upon an optical character recognition of the alphanumeric text to determine the medication within each compartment based upon the respective compartment image, and determine a discrepancy between the determined medication within each compartment and the desired respective medication within each compartment, and upon determining the discrepancy, generate a display notification for display on a display carried by the housing, the display notification including an image of the medication tray including the plurality of compartments and the medications within each compartment and with visual indicators corresponding to each compartment overlaid on each compartment in the image of the medication tray, each visual indicator having one of a first visual characteristic indicative of the discrepancy and a second visual characteristic different than the first visual characteristic indicative of no discrepancy.

14. The method of claim 13 wherein using the processor comprises using the processor to determine whether the respective medication within each compartment has expired based upon the respective compartment image, and upon determining the respective medication has expired, generate an expired medication display notification that includes an expired medication visual indicator corresponding to each compartment determined to have expired medication.

15. The method of claim 13 wherein using the processor comprises using the processor to determine whether the respective medication within each compartment has been recalled based upon the respective compartment image, and upon determining the respective medication has been recalled, generate a recalled medication display notification that includes a recalled medication visual indicator corresponding to each compartment determined to have recalled medication.

16. A non-transitory computer readable medium for managing medication in a medication inventory system comprising a medication tray comprising a plurality of partitions defining a plurality of compartments, the medication tray having a computer-readable tray identifier associated therewith, and each compartment for storing a respective medication, the non-transitory computer readable medium comprising computer executable instructions that when executed by a processor cause the processor to perform operations comprising:

cooperating with at least one imaging apparatus carried by a housing of a mobile wireless communications device to determine the computer-readable tray identifier of the medication tray;

maintaining in a memory a desired respective medication within each compartment based upon the tray identifier;

cooperating with the at least one imaging apparatus to obtain a respective compartment image including the medication within each compartment, the respective compartment image comprising alphanumeric text associated with the medication therein;

using machine learning based upon an optical character recognition of the alphanumeric text to determine the medication within each compartment based upon the respective compartment image; and determining a discrepancy between the determined medication within each compartment and the desired respective medication within each compartment, and upon determining the discrepancy, generating a display notification for display on a display carried by the housing, the display notification including an image of the medication tray including the plurality of compartments and the medications within each compartment and with visual indicators corresponding to each compartment overlaid on each compartment in the image of the medication tray, each visual indicator having one of a first visual characteristic indicative of the discrepancy and a second visual characteristic different than the first visual characteristic indicative of no discrepancy.

17. The non-transitory computer readable medium of claim 16 wherein the operations comprise determining whether the respective medication within each compartment has expired based upon the respective compartment image, and upon determining the respective medication has expired, generating an expired medication display notification that includes an expired medication visual indicator corresponding to each compartment determined to have expired medication.

18. The non-transitory computer readable medium of claim 16 wherein the operations comprise determining whether the respective medication within each compartment has been recalled based upon the respective compartment image, and upon determining the respective medication has been recalled, generating a recalled medication display notification that includes a recalled medication visual indicator corresponding to each compartment determined to have recalled medication.

* * * * *